US008848988B2

(12) United States Patent
Plickert et al.

(10) Patent No.: US 8,848,988 B2
(45) Date of Patent: Sep. 30, 2014

(54) APPLIANCE AND METHOD FOR EVALUATION AND ASSESSMENT OF A TEST STRIP

(75) Inventors: Volker Plickert, Brieselong (DE); Lutz Melchior, Berlin (DE); Wilko Hein, Berlin (DE); Thorsten Jödicke, Berlin (DE)

(73) Assignee: Optricon GmbH, Berlin (DE)

( * ) Notice: Subject to any disclaimer, the term of this patent is extended or adjusted under 35 U.S.C. 154(b) by 641 days.

(21) Appl. No.: 13/129,508

(22) PCT Filed: Nov. 16, 2009

(86) PCT No.: PCT/DE2009/001607
§ 371 (c)(1),
(2), (4) Date: Aug. 23, 2011

(87) PCT Pub. No.: WO2010/054645
PCT Pub. Date: May 20, 2010

(65) Prior Publication Data
US 2011/0293153 A1 Dec. 1, 2011

(30) Foreign Application Priority Data
Nov. 14, 2008 (DE) .......................... 10 2008 058 132

(51) Int. Cl.
G06K 9/00 (2006.01)
G01N 21/84 (2006.01)
(52) U.S. Cl.
CPC ................................. G01N 21/8483 (2013.01)
USPC ........................................................ 382/128
(58) Field of Classification Search
USPC ........................................ 382/128, 133, 134
See application file for complete search history.

(56) References Cited

U.S. PATENT DOCUMENTS

| 5,408,535 | A | * | 4/1995 | Howard et al. ................ 382/128 |
| 6,012,390 | A | * | 1/2000 | Ott et al. ......................... 101/365 |
| 6,136,610 | A | * | 10/2000 | Polito et al. ..................... 436/514 |

(Continued)

FOREIGN PATENT DOCUMENTS

| EP | 1 843 147 A1 | 10/2007 |
| EP | 1 936 362 A1 | 6/2008 |
| EP | 1 965 199 A1 | 9/2008 |

OTHER PUBLICATIONS

International Search Report (PCT/ISA/210) issued on Jun. 21, 2010, by German Patent Office as the International Searching Authority for International Application No. PCT/DE2009/001607.

*Primary Examiner* — Aaron W Carter
(74) *Attorney, Agent, or Firm* — Buchanan Ingersoll & Rooney PC

(57) ABSTRACT

The invention relates to a method for quantitative determination of test results from diagnosis methods with the aid of an optoelectronic evaluation appliance, and to the evaluation appliance itself, characterized in that the digital pixel information per color level or grey level is represented in its intensity in the microprocessor as one column per pixel, wherein the column height corresponds to the intensity, and these columns are displayed alongside one another on one plane, such that the intensity distribution is displayed over the test area as a surface contour or surface profile, the height profile of which corresponds to the intensity profile of the color intensity received by the CCD. Fields of application for the invention are test methods in biochemical laboratories, such as medical diagnosis, forensic medicine, foodstuff diagnosis, molecular biology, biochemistry, gene technology and all other related fields, as well as patient monitoring for home users or in pharmacies.

20 Claims, 10 Drawing Sheets

(56) References Cited

U.S. PATENT DOCUMENTS

| | | | |
|---|---|---|---|
| 6,178,254 B1* | 1/2001 | Rappette et al. | 382/112 |
| 6,267,722 B1* | 7/2001 | Anderson et al. | 600/300 |
| 6,394,952 B1* | 5/2002 | Anderson et al. | 600/300 |
| 6,514,461 B1* | 2/2003 | Lappe et al. | 422/68.1 |
| 6,716,393 B2* | 4/2004 | Lappe et al. | 422/68.1 |
| 6,867,051 B1* | 3/2005 | Anderson et al. | 436/518 |
| 6,936,476 B1* | 8/2005 | Anderson et al. | 436/518 |
| 6,964,752 B2* | 11/2005 | Lappe et al. | 422/82 |
| 7,097,103 B2* | 8/2006 | Tseng | 235/462.13 |
| 7,197,169 B2* | 3/2007 | Wang | 382/128 |
| 7,270,970 B2* | 9/2007 | Anderson et al. | 435/7.94 |
| 7,344,081 B2* | 3/2008 | Tseng | 235/462.13 |
| 7,537,733 B2* | 5/2009 | Lappe et al. | 422/82.05 |
| 7,623,240 B2* | 11/2009 | Rudolf | 356/402 |
| 7,776,618 B2* | 8/2010 | Nazareth et al. | 436/518 |
| 7,822,245 B2* | 10/2010 | Wang | 382/128 |
| 7,885,444 B2* | 2/2011 | Wang | 382/128 |
| 7,943,381 B2* | 5/2011 | Lappe et al. | 436/56 |
| 8,068,666 B2* | 11/2011 | Gregory et al. | 382/162 |
| 8,072,494 B2* | 12/2011 | Qiu et al. | 348/189 |
| 8,202,729 B2* | 6/2012 | Lappe et al. | 436/56 |
| 8,211,711 B2* | 7/2012 | Nazareth et al. | 436/514 |
| 8,268,636 B2* | 9/2012 | Nazareth et al. | 436/514 |
| 8,455,257 B2* | 6/2013 | Lappe et al. | 436/56 |
| 2002/0081233 A1* | 6/2002 | Lappe et al. | 422/82.05 |
| 2004/0043502 A1* | 3/2004 | Song et al. | 436/172 |
| 2004/0095360 A1* | 5/2004 | Tseng et al. | 345/619 |
| 2004/0125998 A1* | 7/2004 | Wang | 382/129 |
| 2004/0131238 A1* | 7/2004 | Wang | 382/128 |
| 2004/0166023 A1* | 8/2004 | Lappe et al. | 422/68.1 |
| 2004/0232239 A1* | 11/2004 | Tseng | 235/462.01 |
| 2004/0241752 A1* | 12/2004 | Anderson et al. | 435/7.1 |
| 2005/0074362 A1* | 4/2005 | Lappe et al. | 422/68.1 |
| 2005/0095697 A1 | 5/2005 | Bachur, Jr. et al. | |
| 2005/0105111 A1* | 5/2005 | Ott et al. | 358/1.9 |
| 2005/0203353 A1* | 9/2005 | Ma et al. | 600/315 |
| 2006/0008923 A1* | 1/2006 | Anderson et al. | 436/518 |
| 2006/0014302 A1* | 1/2006 | Martinez et al. | 436/518 |
| 2006/0094127 A1* | 5/2006 | Tseng | 436/169 |
| 2006/0133956 A1* | 6/2006 | Hamanaka | 422/68.1 |
| 2006/0176483 A1* | 8/2006 | Rudolf | 356/406 |
| 2006/0240541 A1 | 10/2006 | Petruno et al. | |
| 2007/0003115 A1* | 1/2007 | Patton et al. | 382/128 |
| 2007/0031283 A1 | 2/2007 | Davis et al. | |
| 2007/0048184 A1* | 3/2007 | Lappe et al. | 422/63 |
| 2007/0048875 A1* | 3/2007 | Lappe et al. | 436/164 |
| 2007/0161103 A1* | 7/2007 | Buchmann et al. | 435/287.2 |
| 2007/0196862 A1* | 8/2007 | Wang | 435/7.1 |
| 2007/0223781 A1* | 9/2007 | Wang | 382/100 |
| 2008/0100851 A1 | 5/2008 | Asfour et al. | |
| 2008/0213920 A1* | 9/2008 | Nazareth et al. | 436/536 |
| 2008/0219499 A1* | 9/2008 | Gregory et al. | 382/100 |
| 2009/0304247 A1 | 12/2009 | Petrich et al. | |
| 2010/0261293 A1* | 10/2010 | Nazareth et al. | 436/518 |
| 2010/0267166 A1* | 10/2010 | Nazareth et al. | 436/514 |
| 2011/0208438 A1* | 8/2011 | Lappe et al. | 702/19 |
| 2012/0284054 A1* | 11/2012 | Lappe et al. | 705/3 |
| 2013/0268450 A1* | 10/2013 | Lappe et al. | 705/317 |
| 2013/0273666 A1* | 10/2013 | Chen et al. | 436/169 |

* cited by examiner

View field with defined
Reference field - lighted

Image without
lighting

APPLIANCE AND METHOD FOR
EVALUATION AND ASSESSMENT OF A TEST
STRIP

CROSS-REFERENCE TO RELATED
APPLICATIONS

This application is the United States national phase under 35 CFR §371 of PCT International Patent App. No. PCT/DE2009/001607, filed on Nov. 16, 2009, and claiming priority to German application no. DE 10 2008 058 132.1, filed on Nov. 14, 2008.

BACKGROUND OF THE INVENTION

1. Field of the Invention

Embodiments are in the field of quantitative determination of test results from diagnosis methods. They may have application, for example, in biochemical laboratories, such as medical diagnosis, forensic medicine, foodstuff diagnosis, molecular biology, biochemistry, gene technology, and patient monitoring for home users or in pharmacies.

2. Description of Related Art

Above all in modern medicinal diagnostics, the application of quick tests has greatly gained in significance both for physicians and pharmacists, but also for self-users at home.

For example, in in-vitro diagnostics, so-called lateral flow assays are used in order to produce diagnoses for patients. For this, a body fluid (blood, urine, saliva, sweat) is taken from a patient and applied to a field provided for this purpose on a carrier card or cassette. FIG. 8 shows such a test card or test cassette.

In a card (1) or a cassette (2), as the case may be, there is a test strip (3) made of an absorbent fleece, which is visible through openings (4) and (5). A body fluid (blood, saliva, urine) taken from the test person is applied to these openings. The body fluid spreads on the test strip and flows in the direction of the visible opening (6) thanks to the capillary forces. On the strip, reagents have been applied in stripe-like lines vertical to the direction of flow (antibodies), the proteins from the body fluid reacting with them.

In the view field, there is a colour change reaction on a first line (7)—the capture line, displaying the concentration of the body-own protein in the body fluid to be detected. The sample fluid moves forward to a second line, the control line, and displays the validity of the test.

The tests are based on antibody reactions of specific proteins in the blood.

As a matter of principle, a distinction is made in the lateral flow assays between competitive and non-competitive tests: in non-competitive LFA's, the intensity of the test signal increases with the increased concentration of the analyte. In competitive LFA's, a reduction of the intensity of the test signal comes about in an increase of the concentration of the analyte: with a strong analyte concentration, the control line colours increasingly weakly.

A plethora of such tests with quantitative and qualitative detection exists. In each case, a certain threshold concentration exists, which is detected by means of a colour signal, in which context the statement that a colour change has even taken place is sufficient in qualitative tests (e.g. pregnancy tests) m whereas the analyte concentration correlates with the colour intensity within the test zone (control line) with the analyte concentration. The invention exclusively relates to the detection of quantitative tests. In this context, each test has a specific, yet precisely reproducible interconnection between analyte concentration and colour intensity.

For example, in a heart attack, the protein h-FABP is released into the blood in a concentration of a few nl and can be detected as early as 15 minutes after the infarction. If a drop of blood of a few nanoliters (nl) is placed on the sample field, the following reaction takes place on the test card:

The components of the blood are taken apart (so-called blood plasma), as a result of capillary forces, the h-FABP reaches the antibody line and reacts there with gold-labelled antibodies. They move on to the capture line. In the capture line, a discoloration is triggered, in which context the strength of the discoloration (i.e. the colour intensity) is a measure for the quantity of antibodies. The strength of the infarction results in differing protein concentrations, which in the end causes differing colour intensities of the capture lines: a slight colour intensity means a slight infraction, a strong colour intensity indicates a severe infraction. The coloured antibodies flow on to the control line, which signalises whether the test is valid or not.

So the assessment of the colour intensity gives information about the severity of the incident.

Such tests with quantitative assessment exist in the meantime for various health diagnoses, in the end giving information about the patient's point of care. The biologists' vision is diagnosing or predicting not only heath "incidents" which have already taken place, but also ones forthcoming for the body. In future, it is also to be possible for various diagnoses to be obtained from a small amount of blood or other body fluids on a joint card. The market prospects also appear to be very great because people are increasingly willing to invest in health.

In all these cases, precise quantification of the test result is of great importance.

A number of evaluation devices, so-called readers, are already known for quantitative assessment from the state of the art. For example, EP 1965199 describes an evaluation device for the evaluation of a test sample, in which context electromagnetic radiation of a source of radiation falls onto a test sample inserted into the device, the reflected radiation passes through an opening and is deflected onto the measurement device.

The measurement device described in EP 1965199 and generally customary is a camera system with commercial image recognition and evaluation. Such systems use customary CCD cameras, in which context the images are portrayed in video systems with commercial operating systems. Said systems are available in large quantities. The systems portray the image on a screen, in which context the test strips are portrayed with few pixels (depending on the image evaluation). The colour intensity is evaluated by the colour intensity of the pixels portraying the test strip being analysed in a specific programme. The assessment of the colour intensity depends on a large number of parameters (white balance, lighting etc.). In these methods, the evaluation is however very imprecise. The problem is the precise determination of the concentration of the antibodies, which is mainly caused by the fact that the test strips do not react homogeneously.

A suggestion to solve this problem is disclosed in document US 2005/0095697. In it, the signals are portrayed on CCD lines with direct electronic actuation. In the use of the CCD and direct actuation (slide register), each of the individual photo diodes can be read out directly. As each individual photo diode recognises 256 differing colour intensities, the signal portrayed can be precisely distinguished in 256 grey levels.

The advantage of the direct electronic actuation is that the grey levels are read out directly and, for example, compared with the value which, for example, a white background provides. This solution with a CCD line provides the advantage that the CCD information is processed directly. On the other hand, the electronic efforts are higher than with the commercial systems. One has to acquaint oneself with the direct microprocessor programming. On the other hand, one has the benefit that the entire software necessary can be accommodated in the microprocessor of a mobile appliance and the commercial operating system and permanent software updates can be waived.

But as a line cannot provide an extensive image resolution, a movement of the test field in the transverse direction to the line is necessary for evaluation with the appliance according to US 2005/0095697, this being implemented by detection during the insertion of the card into the shaft. The problematic thing in this context is that the user pushes the card into the shaft at the right speed or the sensor works quickly enough. In this way, this method is also imprecise and the results are not sufficiently reproducible.

An essential difficulty in quantitative diagnoses is thus that, on the one hand, the quantity of antibodies is to be quantified (unlike the test with "digital" statements, e.g. pregnant, yes or no), but, on the other hand, the test strips do not react homogeneously. The causes of this are varied, the concentration in the substance to be applied is not homogeneous, application is not done homogeneously, the position of the control or capture line in the test field is not the same, the line geometry deviates etc.

"AntiAging"

A further problem with the devices is that the measurement reproducibility must be guaranteed over the entire life cycle of the appliance and under various ambient influences (temperature, air humidity). This means that test with the same colour identity must result in the same measurement values under various operating temperatures and also after a number of years. This is technically counteracted by the fact that the lighting elements in the appliance age, with the result that the optical performance decreases in the course of time with constant electricity and in addition the optical performance is a function of the appliance temperature. The receiving components (CCD) manifest a certain dark current and inherent noise, as a result of which the measurement precision is limited. These variables are a function of the temperature and time.

In high-quality laboratory devices, this has been solved by the fact that either the lighting strength of the sources of light is regulated via a monitor function (e.g. a photo diode) and/or the CCD is additionally kept at a constant temperature. For this, it is placed on a Peltier element. A Peltier element cools or heats the carriers, as the case may be. Such elements are comparatively expensive and consume large amounts of electricity, with the result that the use of Peltier elements for tempering in mobile devices is difficult to implement.

"Calibration"

A further difficulty is guaranteeing measurement precision in various appliances for the same test and with differing test batches: there must be a guarantee that the same tests (same type) also provide the same results with differing test batches measured with differing devices. This is guaranteed in high-quality appliances (laboratories) by the fact that a storage medium is enclosed with the tests per batch, containing batch-specific data and being assigned to the test. This problem has yet to be solved for mobile appliances.

"Test Identity"

The number of different tests is permanently increasing. This is why appliances have increasingly been designed for a number of tests. Before starting the measurement, the operator must input the test being measured and also state the results which can be expected. In the appliance, the calibration curves, i.e. the interconnection between measured colour intensity and analyte concentration in the body fluid, have been deposited in the memory for the listed tests. The appliance then accesses experience figures or value tables stored in the appliance. The particularly dangerous thing in this context is that the test identity is mixed up, i.e. a wrong test can be called. This is why it is desirable for the appliance to recognise the kind of test automatically.

"Upgrade Ability"

Up to now, appliances have been designed and calibrated in the factory for certain tests. The appliances cannot be extended for additional tests. Such additional new tests can differ from the existing ones, for example, in various value tables in the allocation between measured colour intensity and analyte concentration in the body fluid and can also manifest differing light absorptions as a result of differing colours in the conversion reaction in the capture line.

BRIEF SUMMARY OF THE INVENTION

Customers would like appliances which can be retrofitted for the new tests without the appliances having to be sent back to the manufacturer in a time-consuming way.

Thus, the invention was based on the following task of providing a mobile hand-held appliance which is to manifest the following benefits:

1. providing an improved evaluation procedure and appliance for its performance, supplying reliable and reproducible quantitative results with an improved measurement precision and with a reduced susceptibility to disturbances;
2. improvement of the measurement reproducibility for the lifetime of the appliance, there must be a guarantee that the appliance measures the same values after a number of years (anti-aging);
3. appliance defects or optical losses of adjustments can be recognised and corrected automatically (self-test);
4. that the measurement values do not fluctuate between various devices, i.e. differences between appliances can be compensated (calibration);
5. that the appliances can be used for a number of differing tests, in which context the tests should be recognised automatically by the appliance at the same time, in order to rule out mix-ups (automatic recognition of test identity):
6. the appliances should be freely programmable and retrofittable for additional tests (upgrade ability).

The essential prerequisite of the invention is the use of a CCD matrix as reception element and the fact that the entire image of the test strip is recorded without a relative movement between test card and appliance and is directly recorded and processed by a microprocessor.

DETAILED DESCRIPTION OF THE INVENTION

Figure 1:
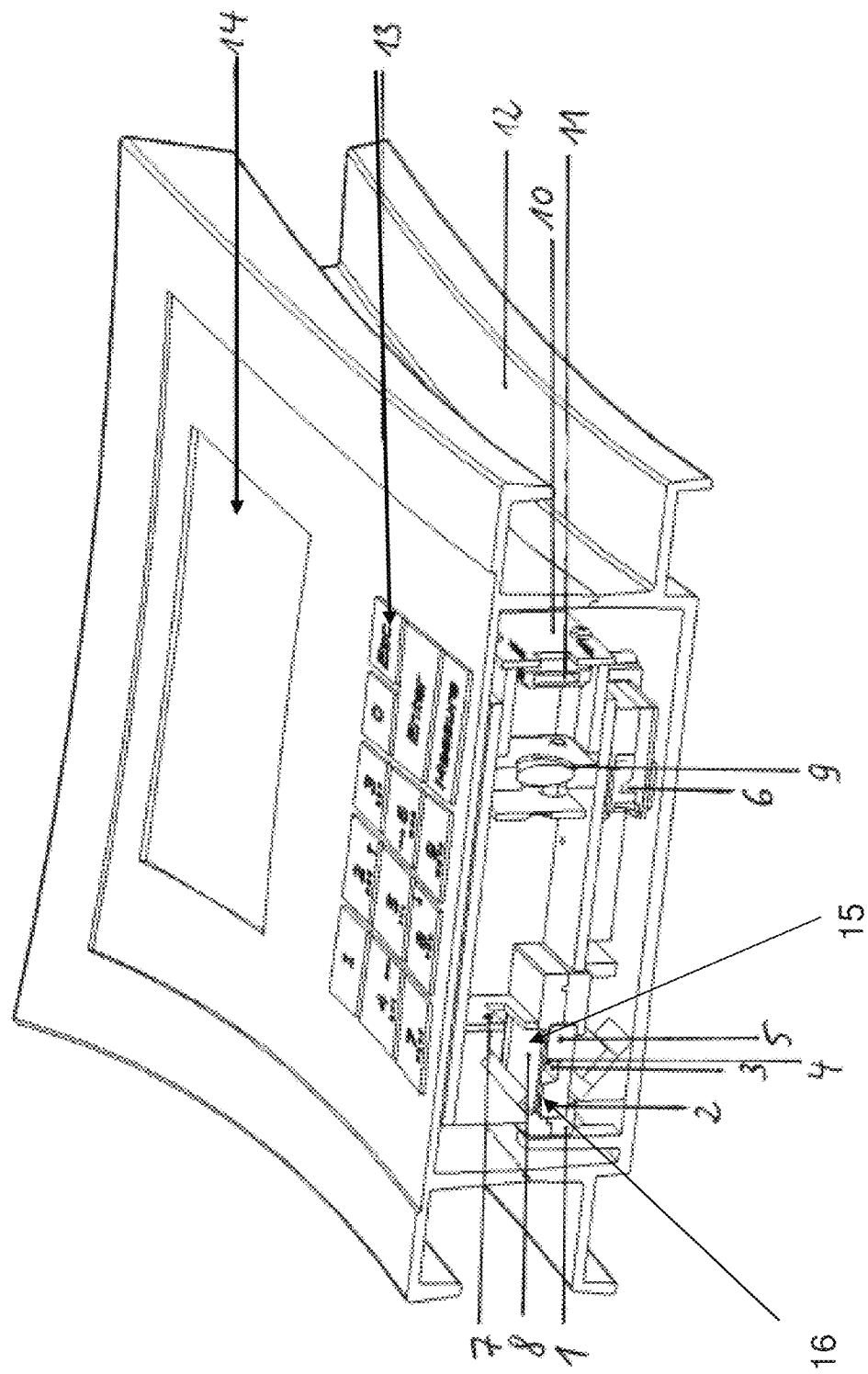
FIG. 1 Schematic portrayal of the appliance
FIG. 2 Principal mode of procedure
FIG. 3 Portrayal of the filtering by means of median filter
FIG. 4 Shows the mean values of the curve for the values added along the capture and control line and the line through the peak minima
FIG. 5A Shows lines of a lateral flow assay as recognised with a conventional CCD matrix and image evaluation FIG. 5B Shows how the grey values are portrayed in the method according to the invention by processing of the digital image information per pixel FIGS. 6A+6B Show the preferential embodiment of the mobile evaluation appliance according to the invention FIG. 7 Image level with image and reference image, top view Reference signs (1) Reference field with maximum colour intensity
  (2) Reference field, minimum colour intensity
  (3) Size surveying reference field
  (4) Colour reference fields
  (5) Peak detection reference field FIG. 8 Lateral flow assay, test card or test cassette Reference signs (1) Card
  (2) Cassette
  (3) Test strip
  (4) (5) Sample opening, peak detection reference field
  (6) Visible opening
  (7) Capture line
  (8) Control line FIG. 9 Evaluation algorithm

As previously noted herein, customers would like appliances which can be retrofitted for the new tests without the appliances having to be sent back to the manufacturer in a time-consuming way.

Thus, embodiments are based on the following task of providing a mobile hand-held appliance which is to manifest the following benefits:
1. providing an improved evaluation procedure and appliance for its performance, supplying reliable and reproducible quantitative results with an improved measurement precision and with a reduced susceptibility to disturbances;
2. improvement of the measurement reproducibility for the lifetime of the appliance, there must be a guarantee that the appliance measures the same values after a number of years (anti-aging);
3. appliance defects or optical losses of adjustments can be recognised and corrected automatically (self-test);
4. that the measurement values do not fluctuate between various devices, i.e. differences between appliances can be compensated (calibration);
5. that the appliances can be used for a number of differing tests, in which context the tests should be recognised automatically by the appliance at the same time, in order to rule out mix-ups (automatic recognition of test identity):
6. the appliances should be freely programmable and retrofittable for additional tests (upgrade ability).

The essential prerequisite of the invention is the use of a CCD matrix as reception element and the fact that the entire image of the test strip is recorded without a relative movement between test card and appliance and is directly recorded and processed by a microprocessor.

The heart piece of the invention is the surprising establishment that the increase of the measurement precision and measurement reproducibility of lateral flow assays with quantitative message are based on a change of the colour contrast and that this change of the colour contrast can further be implemented by the following features: the use of a CCD matrix with direct evaluation of all pixel figures in precisely quantifiable colour levels (256 levels or more) and their direct evaluation by a microprocessor, optimisation of the colour levels by controllable lighting, portrayal of the colour levels in a pixel mountain range/surface mountain range as a virtual concentration image of the antibody reactions, an algorithm which automatically finds the strips with the sample at rest (no scanner functions, no mechanical error susceptibility) and an automatic finding of the maximum and "calculation" of errors (contaminations) and lacks of homogeneity.

As the total quantity of the antibodies applied is equal in its sum, the invention is based on the idea of "integrating" via the sum total of the reacting and discoloured antibodies.

For this, the entire field of the signal is portrayed onto a CCD matrix. The test strips are portrayed as a "pixel mountain range", in which context the pixel height is proportional to the detected colour levels of the individual pixels.

An intelligent evaluation algorithm is carried out, which finds the test strips to start with by means of scans running orthogonal to one another through the mountain range (maximum), defines an area which defines the test strip as surfaces to be detected and integrates via the colour levels of all these pixels and forms the mean value).

Figure 7:
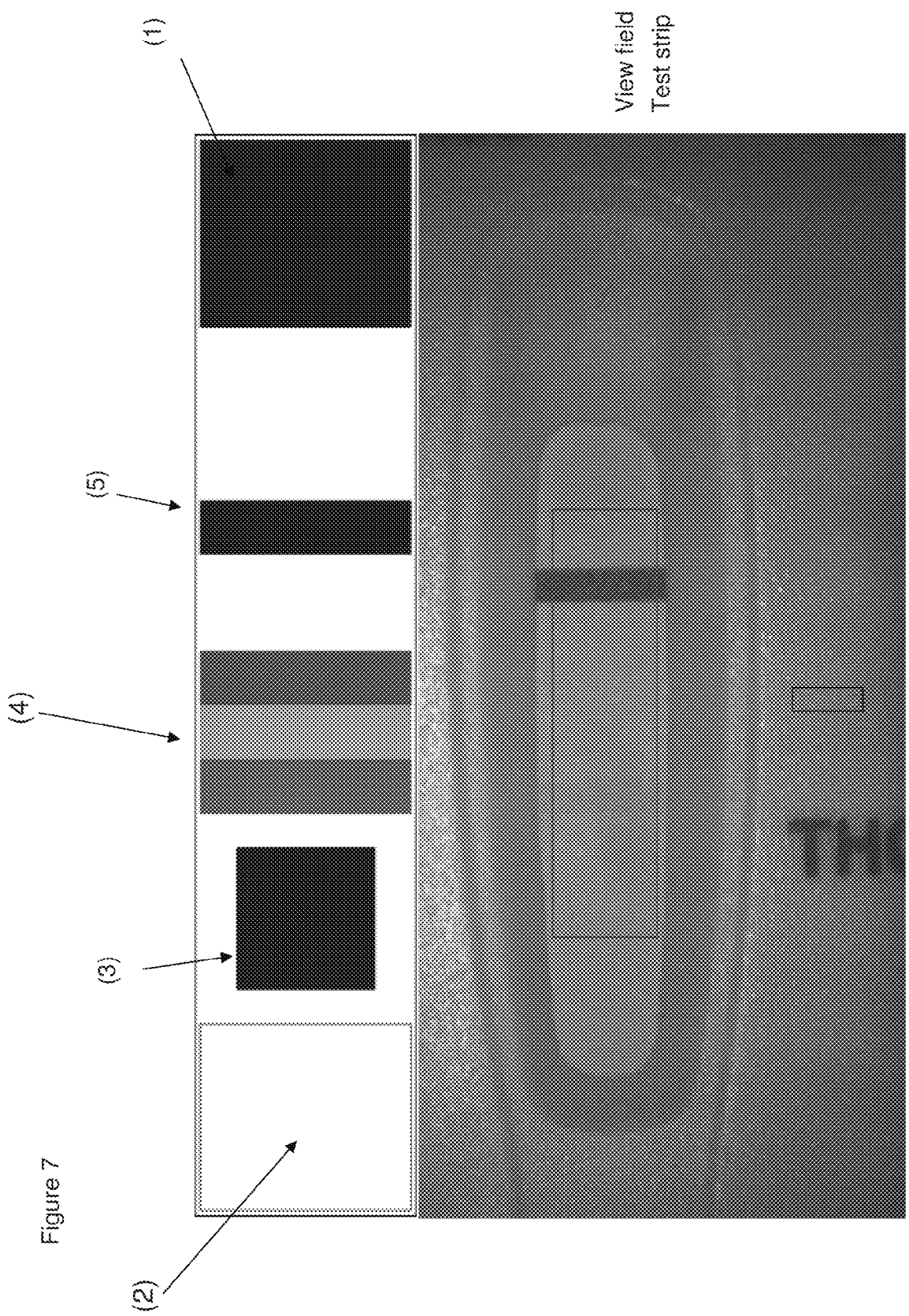
Figure 8:
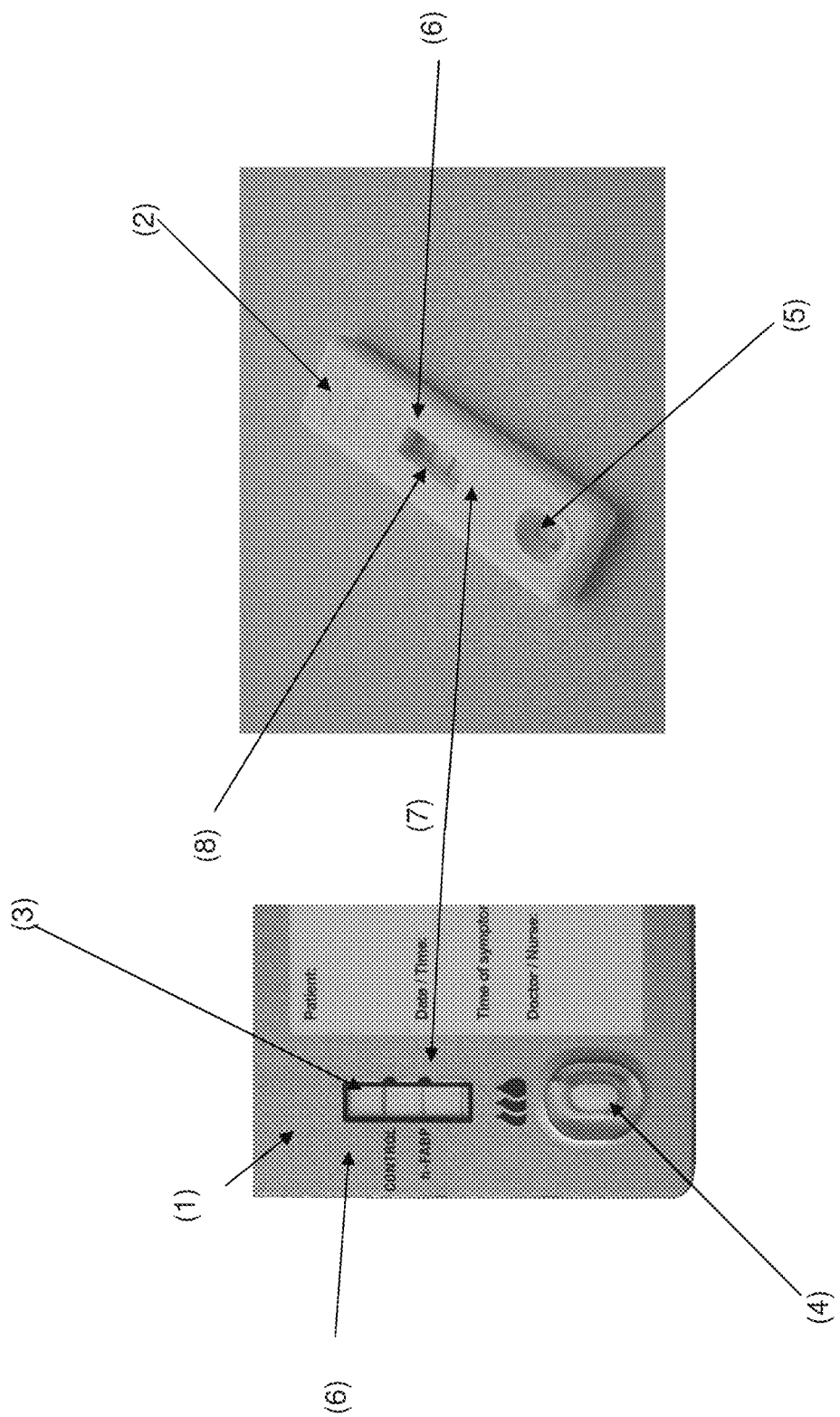

For the assessment of these integrated values, comparative values must be provided, these being equal independent of fluctuations of the lighting or the reception sensitivity. In experience, this is solved by reference fields or reference images not subject to aging effects being arranged in the appliance on the optical object level next to the test field to be detected. This reference field is recorded by the CCD at the same time as the picture of the sight field of the test with capture line and control line. This field has been shown in a top view in FIG. 7. This reference field has a field with a maximum (1) and a field with a minimum (2) colour intensity on the outer edges. These fields are used to scale the reception figure between maximum and minimum figure. Further, the reference field contains a variable measurement reference field (3). It is used to scale the reception surface. As its dimensions are precisely known, the capture line dimensions can be scaled in the same image field independent of the portrayal scale. Further, the field contains colour reference fields in the RGB colours (4). If these are illuminated by various RGB colour sources, various colour intensities are detected on the CCD and the colour values can thus be referenced. In addition, there is also a "peak detect reference field" (5) on the reference field, with which the peak width and location can be referenced. With these test fields, self-calibration (self-test) can be carried out before the start of a test on the test field in the appliance.

With the outside fields, the colour intensity and brightness are calibrated. As it has been excluded from fluctuations, the appliance is independent of fluctuations of the lighting strength, aging of the light sources or the receiver. With the size survey field, image corrections can be carried out if the optic has suffered a loss of adjustment. Colour fluctuations can be compensated with the colour reference field.

In addition, an area for white balance, via which integration is also carried out, is defined, thus forming the comparative figure. This is followed by formation of a difference between pixel integration value and white balance and the comparison of the value with a calibration value stored in a database and then output as a measured value. Optionally, the result can also be output in a three-dimensional portrayal of the test strips.

An appliance for the evaluation of such a test strip essentially comprises an insert, into which the test strip, preferably located in a test card or cassette, is inserted, an optic, which portrays the image of the test strip on a receiver, the reception component, lighting for the test strip, the evaluation electronics and a display. Further, such an appliance must manifest an energy supply and electrical interfaces. Further components are imaginable. The input of values and operation of the appliance are via a keyboard or a touch display. Everything has been accommodated in a joint housing.

The appliance has been designed as a mobile and standalone appliance. The system is completely controlled by its own internal software. Connection to additional devices such as external control computers (laptop) etc. is thus not necessary.

FIG. 1 shows a schematic portrayal of the appliance:

In the insert (1), a cassette (2) with a test strip (3) has been inserted, the test strip being arranged in the field of a recess (4) of the cassette. In addition, said card manifests a recognition label, e.g. a barcode or data matrix code, which can be fitted, for example, on the underside of the card. The label is detected by the scanner (6) via a deflection mirror (5). With the label, the test is identified and assigned to the test deposited in the database or microprocessor or memory.

The test strip in the test field (4) is illuminated by a source of light (LED's) on the illumination board (7). The optical portrayal is done via a deflection mirror (8) and an objective (9). The reception unit comprises a reception board (10), on which the CCD sensor (11) has been fitted. What is not visible is the electronic actuation of the CCD on a circuit board with microprocessor, the energy supply, the batteries. All the components have been fitted in a stable housing (12), which manifests a foil keyboard (13) for operation guidance and a display (14) to show the measured values and the menu guidance in the embodiment.

Between the cassette insert above the cassette, there is a transparent disk (15), through which the test strip is portrayed. On this disk, the reference field (16) which is portrayed in the image directly next to the test strip has been arranged—see FIG. 1.

The test strip is illuminated by the LED's. The image of the test field in the circuit board is portrayed via the mirror through the recess of the illumination board by means of the lens on the CCD sensor. The image information on the CCD sensor is read out controlled via the microprocessor and further processed.

In the implementation of the method, tests strips in which body-specific substances, in particular proteins released in a certain incident in the body, are detected with the help of labelled antibodies are evaluated. The concentration of the labelled antibodies is determined by a colour change in a strip, in which context the colour intensity is proportional to the concentration of the antibodies per volume. For this, the test strip is portrayed with the help of an optic onto a CCD, which comprises pixels areally arranged on a level (quasi individual photo diodes).

Per pixel, the intensity is used in certain, discreetly portrayable colour or grey levels, the information being processed directly.

The relative discolorations are compared with calibration figures deposited in the programme, preferably only values of "line scans" being used. Use with the values obtained from the integration is also imaginable.

Experience has shown that the digital pixel information per colour or grey level in the microprocessor is portrayed as a column per pixel in its intensity, in which context the height of the column matches the intensity, and these columns are portrayed next to one another on a level, with the result that the distribution of the intensity over the test field is portrayed as a surface contour or surface profile, the sequence of the height of which matches the sequence of the colour intensity received with the CCD.

By means of this surface contour or this surface profile, the location of the test strip to be evaluated is recognised with a single, linear scan vertical to the expected strips to be detected, with the result that the location recognition of the test strip field is done simply, quickly and without additional mechanical relative movement between the detector and the test field (for example by a mechanical scanner).

In accordance with the invention, a further linear scanning vertical to the first one is carried out in the area of the strip to be evaluated. This is used for recognition of local changes of intensity. In this way, it is ruled out in the further course of the method that the fluctuations in intensity lead to measurement imprecisions. The location of the first scan is thus corrected such that it passes through the maximum of the test strip.

In accordance with the invention, certain demarcated areas within the test field in which there is formation of sum and mean values by integration over the grey levels of all the pixels contained therein are defined. In this, an area is defined for a section of the test strip such that no colour reaction is expected in it. This value acts as a basic value for later comparisons. For the areas in which colour reactions are expected on the basis of the first line an, a sum value and a mean value are calculated and placed into relation to the sum and/or mean value from the area without colour reaction. From the ratio, a value for the concentration of the protein is calculated in comparison with known calibration figures. As the sum and mean values have originated through integration and the sum of the partial colour reactions in the test strip is proportional to the sum quantity of labelled antibodies, a considerably higher measurement precision is achieved with the integration than in "customary" line scans.

In a particular embodiment of the invention, the digital pixel information is output in a three-dimensional portrayal of the test strips as a virtual concentration image of the antibody reactions as the outcome.

With this portrayal as a surface relief, the person evaluating is given essential knowledge and information in one image at a glance, containing the significance of the measurement result (height), the test fluctuations and possible fluctuations induced by the method.

Thanks to this areal portrayal in combination with the expected outcome, which is a test strip and not individual dots which could possibly come from a surface disturbance or contamination or a "pixel error" of the CCD, it is possible to reduce disturbances which could falsify the measurement result by using corresponding software.

In a particular embodiment of the invention, the areal portrayal has been further processed, preferably by the coloration of certain values, with the result that, for example, a three-dimensional portrayal is achieved.

The method according to the invention is further characterised in that each of the individual photo diodes is directly actuated and read out in the CCD matrix sensor. The digital pixel information can be reproduced according to the invention with the help of any number of grey levels (2 exp x). Preferably, the pixel information is reproduced with the help of 32 to 16777216 colour levels, particularly preferably with the help of 256 colour levels and quite particularly preferably with the help of 4096 grey levels.

In a preferential variant, the colour levels are optimised by a controllable lighting.

As initial substances, body fluids or solutions containing components from body fluids are used according to the invention.

In a particular embodiment of the invention, blood, serum or urine are used as initial materials.

In a preferential embodiment, the method according to the invention is used for the evaluation of lateral flow assays, particularly preferably for the evaluation of lateral flow assays based on antibody antigen reactions with the specific protein h-FABP for recognition of a heart attack.

The invention further relates to an appliance for the method according to the invention.

A preferential embodiment is an appliance for the evaluation of a test strip comprising an insert, an optic, a reception component, lighting for the test strip, evaluation electronics containing an evaluation algorithm, a display, an energy supply and electrical interfaces as well as an output device, characterised in that it portrays the digital pixel information per colour or grey level in the microprocessor in their intensity as column per pixel, with the height of the column matching the intensity, and these columns are portrayed next to one another on one level, with the result that the distribution of the intensity over the test field is portrayed as a surface contour or surface profile, the height profile of which corresponds to the intensity profile of the colour intensity received by the CCD. The invention further relates to the use of this appliance for the method according to the invention.

Thanks to the method according to the invention and the appliance for its performance, an improved possibility of evaluation for diagnostic tests is provided, supplying reliable and reproducible quantitative results with higher precision. The benefits of the invention are, amongst others, the increase of the reproducibility, the finding of the test strips, despite differing locations on the test field, and the output of identical measurement values despite differing capture line geometry (measurement strips for example "run" based on the assumption that the sum total of the particles to be reacted which have been applied is equal in sum and the sum of the discoloured particles is proportional to the concentration of the protein).

In a specific embodiment of the invention, the appliance is suited to evaluating tests of various mathematical sequences between change of the colour intensity and the analyte concentration (polynoms of the $n^{th}$ degree, but constant functions). In this context, the appliances can be used universally, calibration curves being stored in the appliance for the tests in question.

According to the invention, the device excels by the fact that a CCD matrix is used in a mobile appliance with which an image is recorded, which makes the measurement unsusceptible to disturbances. After this, further processing is done with the "close-to-the-hardware" microprocessor and the memory in the appliance, in order to receive a disturbance-free and reliable signal. The universality of the mobile appliance can be extended by new tests additionally being retrofitted by means of a device for code recognition and use of mobile memories (SD card).

Figure 9:
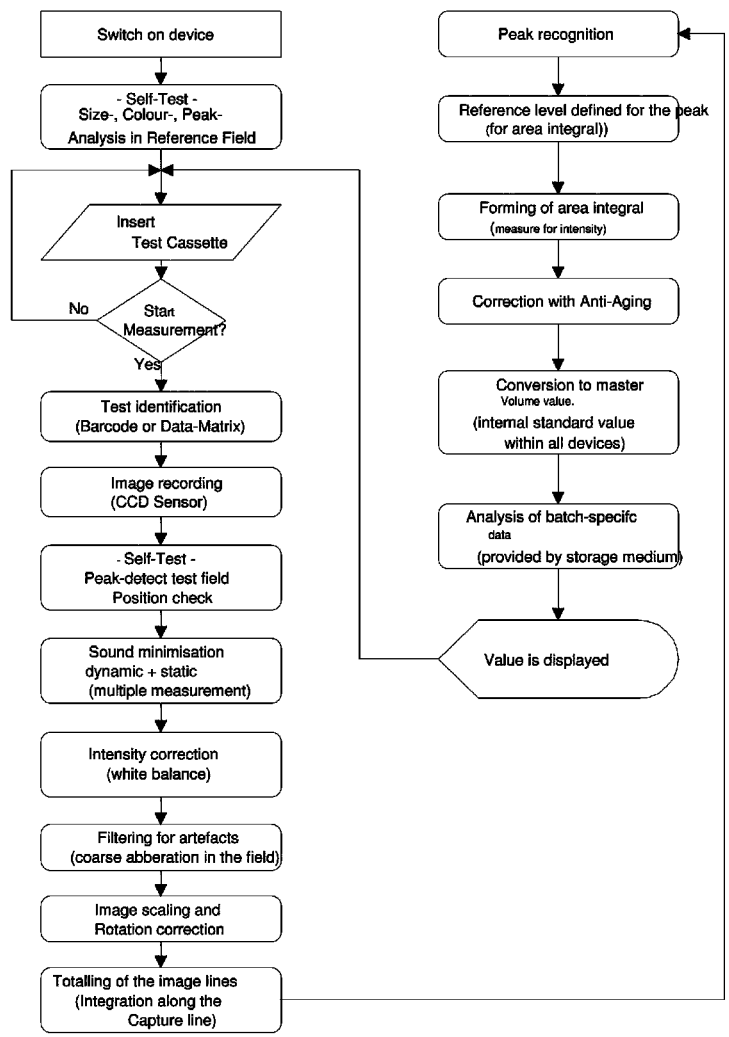

The entire sequence of measurement in the appliance takes place as follows (see FIG. 9):

After the device has been switched on and the test cassette inserted, there is a so-called self-test. In the aforementioned reference field, which is directly next to the measurement object, the colour intensity value are referenced, the image size is referenced and, if applicable, corrected with the values stored in the memory.

The operator starts the measurement and inputs the patients' data.

The appliance identifies the test on the basis of the barcode fitted to the reverse or a data matrix code arranged in the sight field.

The sensor records the images.

A self-test of the peak follows. Is the peak of the control line in the expected test field? If applicable, the field from which the CCD values are recorded is corrected.

For sound minimisation, there is a multiple measurement. It is determined via the values measured, with the result that minimum and maximum values from the noise of the detector are "smoothed".

Intensity correction: a white balance takes place. The measured values for the minimum optical intensity are deducted from the measured values.

With an intensity balance, differences in the lighting of the test field and lighting fluctuations due to aging or temperature fluctuations are compensated.

Figure 2:
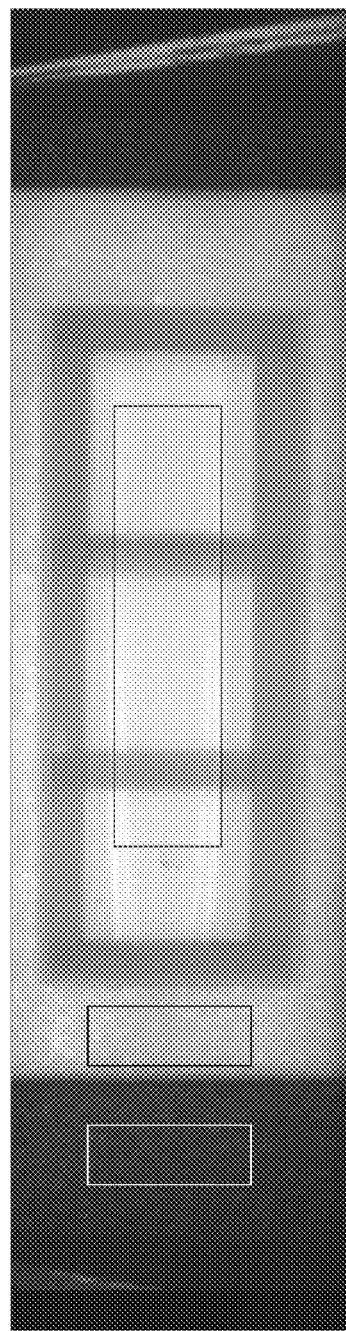
Figure 2:
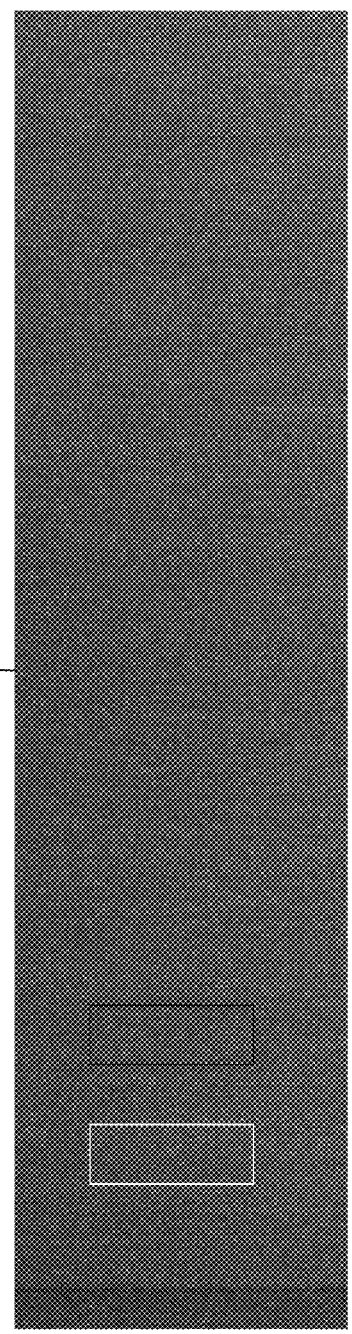

FIG. 2 shows the principal mode of procedure: in the so-called "black balance", the colour intensity values of the individual CCD elements (pixels) occurring without lighting of the CCD as so-called dark current or noise are subtracted.

Filtering for artefacts: the software recognises coarse aberrations in the field, for example contaminations in the test field, and compensates these values.

Figure 3:
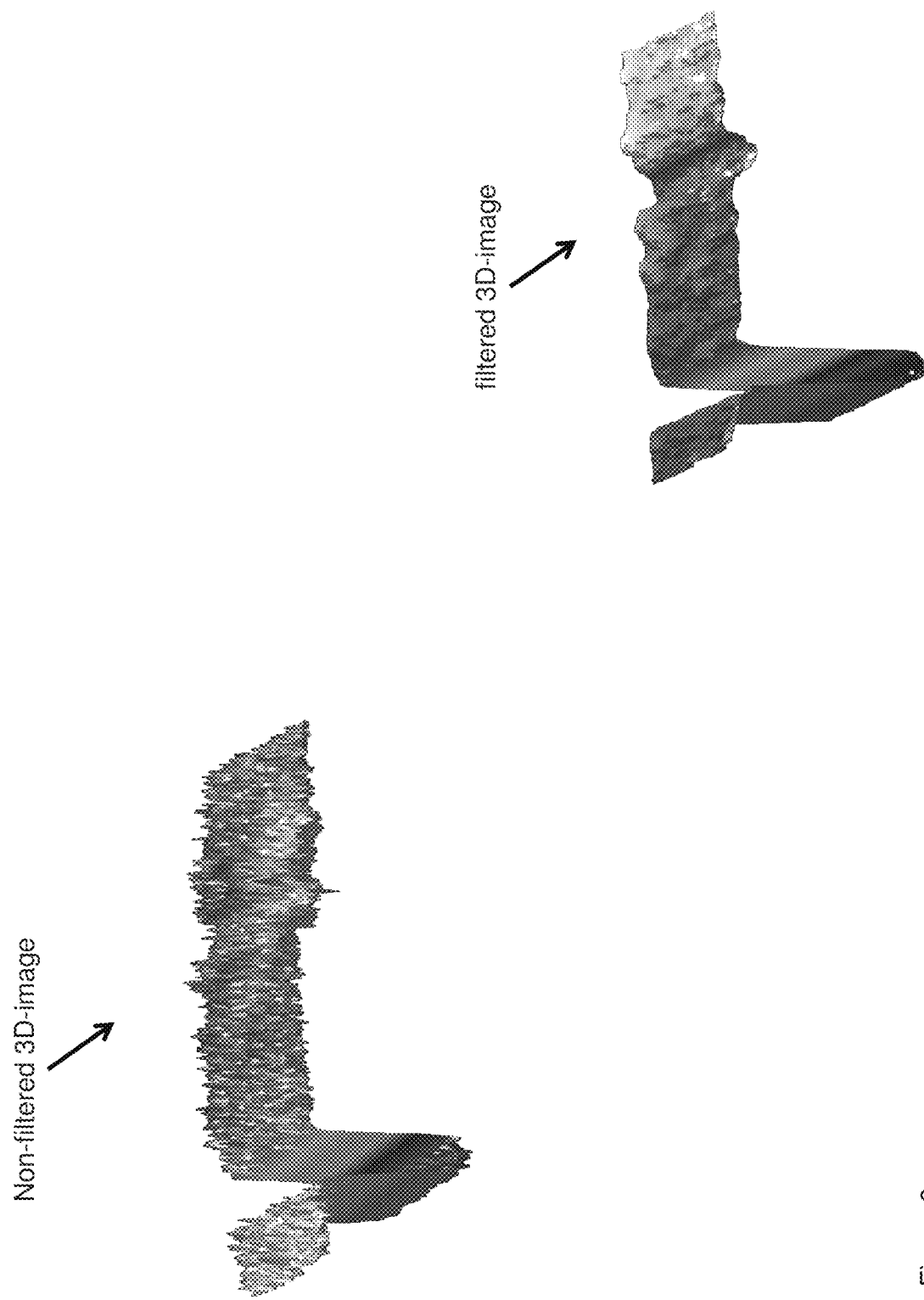

This filtering has been portrayed in FIG. 3. A median filter is used, through which pixel errors are eliminated and residual noise in the image is minimised. The filter degree can be set with the software.

Image scaling and rotation correction: in comparison with the reference fields, there is recognition of whether the capture line is distorted in the test field. This is corrected by a rotation correction.

Totalling of the image lines (integration along the capture line). The image lines are added and mean figures formed.

A peak recognition is carried out.

A reference level is defined for the peak. The reference level defines the intensity values of the environment of the test strip.

Figure 4:
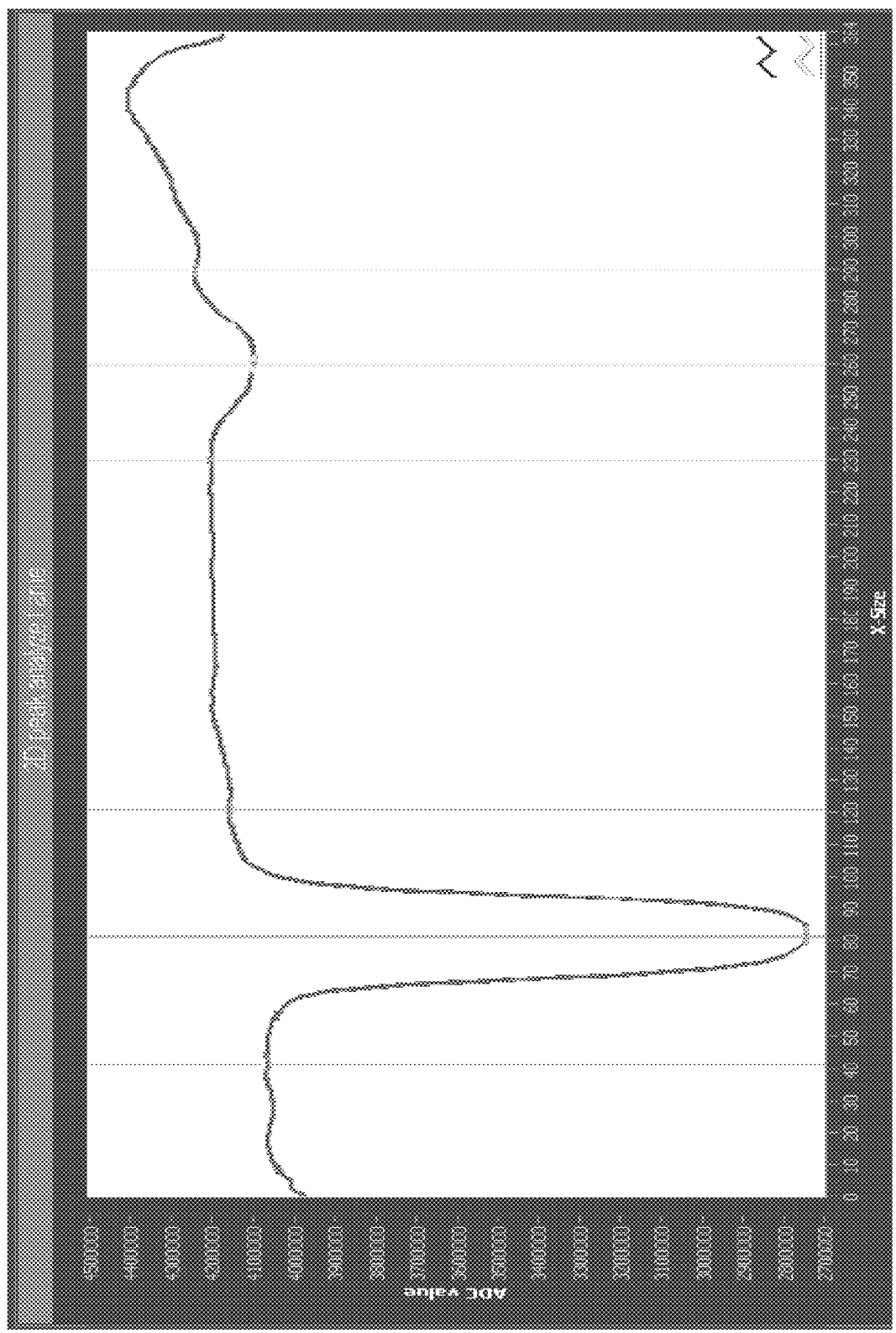

FIG. 4 shows the mean values of the curve for the values added along the capture and control line and the lines through the peak minima.

An area integral for the area between the reference level and the peak is formed. The area integral is a measure for the total colour change in the capture line.

There is a correction with anti-aging. In this, the area integral is compared and standardised with the reference curve between min. and max. value determined in the self-test (black/white balance).

In the memory, a master volume calibration has been deposited in the factory for each appliance. With a set of master cards with precisely defined colour intensity, a value table with correction values is stored in the appliance, with the result that the master cards always display identical values independent of the appliance. In this step, the measured and integrated value is converted to this calibrated master volume value.

Differing tests have test-specific and batch-dependent values. They can be linear or manifest an arbitrary, constant course. These specific data are provided by a storage medium and have been deposited in the appliance. In this step, the master volume values are scaled with the values specific to the test and batch and are calculated.

Finally, this value is displayed.

Further beneficial properties and features of the invention become clear from the following embodiment, which is to act as a non-exhaustive example for explanation.

Embodiment 1

Comparison of a conventional mode of portrayal and the mode of portrayal with the method according to the invention.

Figure 5A:
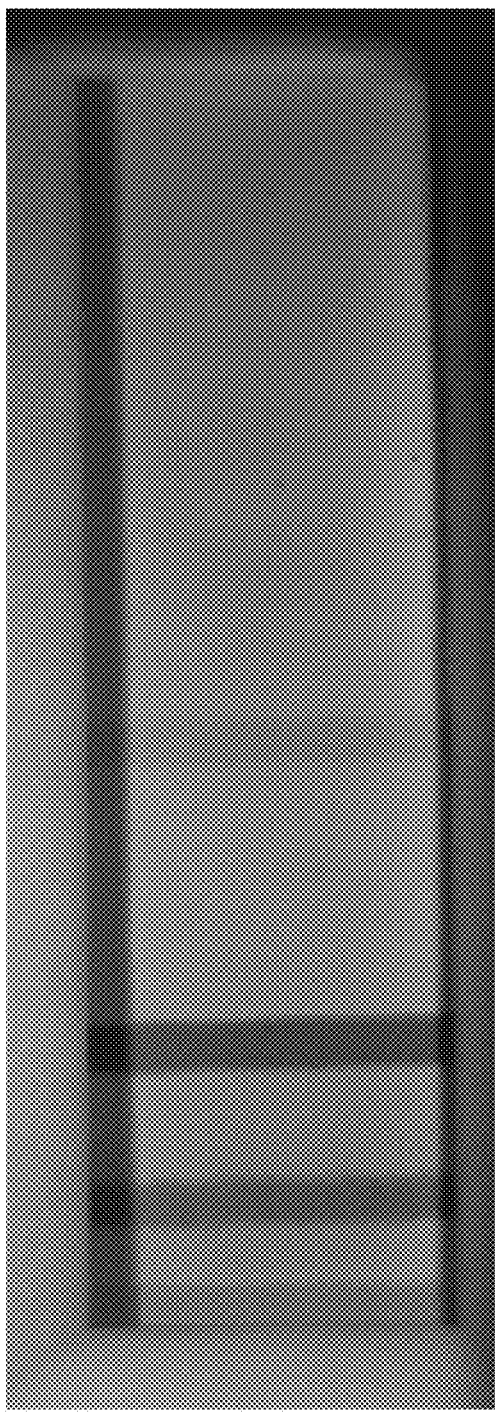

FIG. 5A shows lines of a lateral flow assay as recognised with a conventional CCD matrix and image evaluation.

Figure 5B:
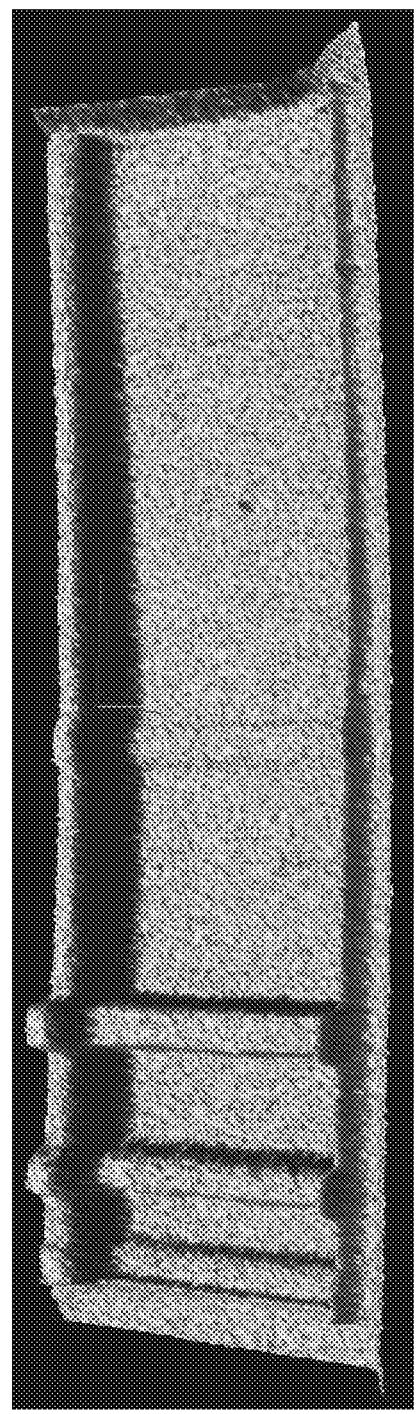

In comparison with this, FIG. 5B shows how the grey values are portrayed in the method according to the invention by processing of the digital image information per pixel:

This mode of procedure shows, on the one hand, the sources of errors in the evaluation of customary methods, as well as the possibility offered from this portrayal which is obtained: any number of cuts can be applied (in order to find the strips, for example). Even the very weak line can be clearly detected. An integration via the individual pixel values is considerably more precise than, for example, only one cut. Even the image arching (caused by the optic) can be corrected by the software.

Embodiment 2

Figure 6A:
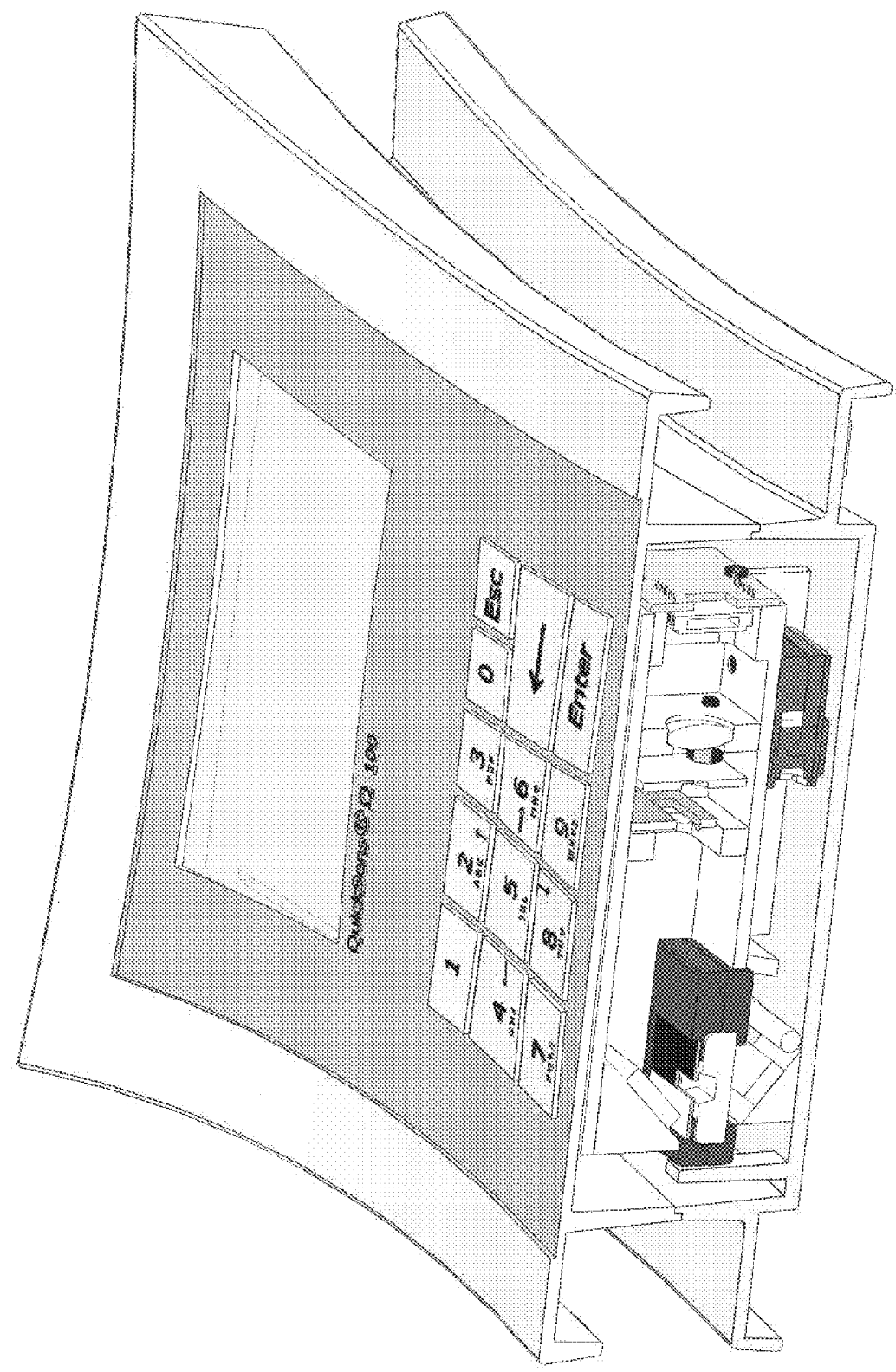
Figure 6B:
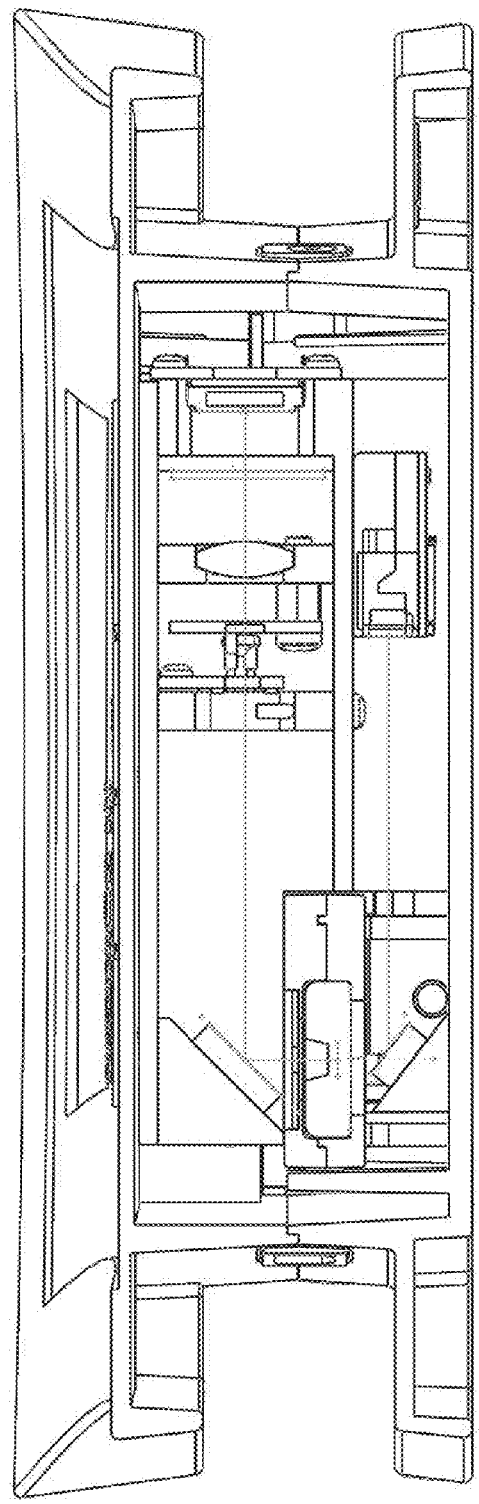

FIGS. 6A and 6B show a preferential embodiment of the mobile evaluation appliance pursuant to the invention. The section through the optical portrayal axis of the optic unit has been shown.

All the features portrayed in the above description, the following claims and the figures are of significance both alone and also in an arbitrary combination for the implementation of the invention in its various embodiments.

The invention claimed is:

1. Method for evaluation of a test strip with an appliance containing an insert, an optic portraying the image of the test strip onto a receiver, reference fields or reference images, as the case may be, a reception component, lighting for the test strip, evaluation electronics containing an evaluation algorithm, a display, an energy supply and electrical interfaces as well as an output device, wherein for the evaluation of a test strip on which body-specific substances, in particular proteins released in a certain incident in the body, are detected with the help of labelled antibodies, the concentration of the labelled antibodies is determined by a colour change in a strip, wherein the colour intensity (grey level) of the concentration of the antibodies per volume is proportional, the test strip is portrayed with the help of an optic on a CCD comprising areally arranged pixels on one level (individual photo diodes), wherein the intensity in certain directly portrayable colour or grey levels is used for the evaluation and the relative discoloration is compared via calibration values deposited in the programme, wherein the digital pixel information per colour or grey level in the microprocessor is portrayed in its intensity as a column per pixel, wherein the height of the column matches the intensity, an evaluation algorithm is carried out, firstly finding the test strip by scans through the peaks running orthogonal to one another (maximum), defining an area defining the test strip as areas to be detected and integrating over the colour value levels of all these pixels and forming the mean value and these columns being portrayed next to one another on one level such that the distribution of the intensity over the test field is portrayed as a surface contour or surface profile, the sequence of height of which matches the course of intensity of the colour intensity received with the CCD, and reference fields and reference images located next to the test field to be detected on the optical object level of the appliance are recorded by the CCD simultaneously with the image of the sight field of the test with capture line and control line, wherein possible error and aging processes are eliminated by the reference fields and reference images in the appliance by a definition of an area for the white balance being carried out, via which there is also integration and thereafter a difference being formed between pixel integration value and white balance and the value being compared with calibration values deposited in a database and being output as a measured value.

2. Method according to claim 1, wherein a self-calibration (self-test) is done before the start on the basis of the reference fields and reference images and that a test identification is carried out.

3. Method according to claim 1, wherein a peak correction, a noise smoothing, an intensity correction, a filtering for artefacts, an image scaling and rotation correction, a peak recognition, an anti-aging correction and/or a master volume calibration are done in order to eliminate possible error and aging processes.

4. Method according to claim 1, wherein:
a) a self-test is carried out after the appliance is switched on and the test cassette pushed in, wherein the image size is referenced in the reference field, the colour intensity values are referenced and, if necessary, corrected with the values deposited in the memory,
b) the measurement is started and the patient's data are input by the operator,
c) the images are recorded by a sensor,
d) an addition of the image lines (integration along the capture line) is done, wherein the image lines are added and mean figures are formed,
e) a peak recognition is carried out, with a reference level being defined for the peak, defining the intensity values for the environment of the test strip
f) this value is displayed.

5. Method according to claim 1, wherein the test is identified on the basis of the barcode attached to the reverse or a data matrix code arranged in the sight field before the measurement by the appliance.

6. Method according to claim 1, wherein recording of the images by the sensor is followed by a self-test of the peak, wherein the point in the test field at which the peak is located is established and the field from which the CCD values are recorded is corrected if need be.

7. Method according to claim 1, wherein:
a multiple measurement is carried out, wherein an averaging over the measured values is done, with the result that the noise of the detector can be equalised and/or
an intensity correction is done by means of a white balance, wherein the measured values for the minimum optical intensity are deducted from the measured values and/or
there is filtering for artefacts, wherein pixel errors and residual noise from the image are minimised by means of a median filter and/or
an image scaling and rotation correction are carried out, wherein a comparison with the reference fields is used to recognise whether the capture line is distorted in the test field and it is corrected by a rotation correction and/or
an area integral is formed for the area between the reference level and the peak, wherein an anti-aging correction is held by comparison of the area integral with the reference curve between minimum and maximum value determined in the self-test (black/white balance) and/or
a master volume calibration is carried out, wherein the measured and integrated value is converted to its calibrated master volume value with master cards inside the appliance with at least one value table with correction values.

8. Method according to claim 1, wherein the location of the test strip to be evaluated is recognised by means of the surface contour or the surface profile with a single linear scan vertical to the expected strips to be detected and/or a further linear scan vertical to the first one is held in the area of the strip to be evaluated for recognition of local changes of intensity and thus the location of the first scanning is corrected such that it runs through the maximum of the test strip.

9. Method according to claim 1, wherein certain demarcated areas within the test field, in which the total and the mean value are formed by integration over the colour value levels of all the pixels contained therein, are defined, wherein an area for a section of the test strip is defined such that no colour change is expected therein and this value is defined as a basic value for later comparisons (so-called white balance) and, for the areas in which a colour change is expected, a sum total value and mean value placed in ratio to the sum and/or total value from the area without colour change are calculated and a value for the concentration of the substance being looked for, preferably protein, is calculated from the ratio in comparison with known calibration values.

10. Method according to claim 1, wherein the portrayal as a surface relief contains the significance of the measurement result (height), the test fluctuations and possible procedure-induced fluctuations and essential knowledge and information are portrayed directly visibly from a portrayal.

11. Method according to claim 1, wherein the areal portrayal is put into connection with the expected outcome and disturbances which could falsify the measurement result such as area disturbances, contaminations or "pixel errors" of the CCD are ruled out by means of a software.

12. Method according to claim 1, wherein body fluids or solutions containing components from body fluids are used as initial materials, preferably from blood, serum or urine.

13. Appliance for evaluation of biological tests with various mathematical sequences between change of colour intensity and analyte concentrations, containing an insert, an optic, a reception element with a, CCD matrix of pixels areally arranged on a level as a reception element, a lighting for the test, at least one reference field independent of aging and temperature in the sight field on the image level next to the sight field of the test, which is recorded simultaneously with the image of the sight field of the test and wherein said reference field or reference image have a field with maximum color intensity, a field with minimum color intensity, a variable measurement reference field, color reference fields in the RGB colors and a peak detect reference field on the outer edges, and which can permanently and directly be put into comparison with the test, evaluation electronics containing an evaluation algorithm, a display, an energy supply and electrical interfaces as well as an output device.

14. Appliance according to claim 13 for evaluation of a test strip containing an insert, an optic, a reception element with a CCD matrix of pixels areally arranged on a level as reception element, a lighting for the test, evaluation electronics containing an evaluation algorithm, a display, an energy supply and electrical interfaces as well as an output device, wherein reference fields or reference images have been arranged on the optical object level next to the test field to be detected.

15. Appliance according to claim 13, wherein a digital pixel information can be portrayed with the appliance per colour or grey level in the microprocessor in its intensity as a column per pixel, wherein the column height matches the intensity, and said columns can be portrayed next to another on one level, with the result that the distribution of the intensity over the test field can be portrayed as a surface contour or surface profile, the sequence of height of which matches the sequence of intensity of the colour intensity received with the CCD.

16. The appliance of claim 13, said appliance implementing a method for evaluation of a test strip with an appliance containing an insert, an optic portraying the image of the test strip onto a receiver, reference fields or reference images, a reception component with a CCD matrix of pixels areally arranged on a level as a reception element, lighting for the test strip, evaluation electronics containing an evaluation algorithm, a display, an energy supply and electrical interfaces as well as an output device, wherein for the evaluation of a test strip on which body-specific substances, in particular proteins released in a certain incident in the body, are detected with the help of labelled antibodies, the concentration of the labelled antibodies is determined by a colour change in a strip, wherein the colour intensity (grey level) of the concentration of the antibodies per volume is proportional, the test strip is portrayed with the help of an optic on a CCD matrix comprising areally arranged pixels on one level (individual photo diodes), wherein the intensity in certain directly portrayable colour or grey levels is used for the evaluation and the relative discoloration is compared via calibration values deposited in the programme, wherein the digital pixel information per colour or grey level in the microprocessor is portrayed in its intensity as a column per pixel, wherein the height of the column matches the intensity, an evaluation algorithm is carried out, firstly finding the test strip by scans through the peaks running orthogonal to one another (maximum), defining an area defining the test strip as areas to be detected and integrating over the colour value levels of all these pixels and forming the mean value and these columns being portrayed next to one another on one level such that the distribution of the intensity over the test field is portrayed as a surface contour or surface profile, the sequence of height of which matches the course of intensity of the colour intensity received with the CCD, and reference fields and reference images located next to the test field to be detected on the optical object level of the appliance are recorded by the CCD simultaneously with the image of the sight field of the test with capture line and control line, wherein possible error and aging processes are eliminated by the reference fields and reference images in the appliance by a definition of an area for the white balance being carried out, via which there is also integration and thereafter a difference being formed between pixel integration value and white balance and the value being compared with calibration values deposited in a database and being output as a measured value.

17. Appliance according to claim 13, wherein it is a mobile and stand-alone appliance.

18. Appliance according to claim 13, wherein it contains a device for identification of test strips, preferably a device for recognition of barcodes or data matrix codes.

19. Appliance according to claim 13, wherein it can be con-figured retroactively for additional tests via mobile memories.

20. Appliance according to claim 13, wherein it contains an internal master calibration.

* * * * *